United States Patent
Mault

(10) Patent No.: US 6,277,645 B1
(45) Date of Patent: Aug. 21, 2001

(54) METHOD AND APPARATUS FOR RESPIRATORY GAS ANALYSIS EMPLOYING MEASUREMENT OF EXPIRED GAS MASS

(76) Inventor: James R. Mault, 1580 Blakcomb Ct., Evergreen, CO (US) 80439

(*) Notice: Subject to any disclaimer, the term of this patent is extended or adjusted under 35 U.S.C. 154(b) by 0 days.

(21) Appl. No.: 09/674,897

(22) PCT Filed: Sep. 3, 1999

(86) PCT No.: PCT/US99/17553

§ 371 Date: Nov. 7, 2000

§ 102(e) Date: Nov. 7, 2000

(87) PCT Pub. No.: WO00/07498

PCT Pub. Date: Feb. 17, 2000

Related U.S. Application Data

(60) Provisional application No. 60/095,092, filed on Aug. 3, 1998.

(51) Int. Cl.[7] ................................................. A61B 5/083
(52) U.S. Cl. ............................ 436/133; 436/136; 422/84
(58) Field of Search ............................ 600/531, 532, 600/538; 436/62, 133, 136, 900; 422/84, 98

(56) References Cited

U.S. PATENT DOCUMENTS

| | | | |
|---|---|---|---|
| 2,630,798 | 3/1953 | White et al. | 128/2.07 |
| 2,826,912 | 3/1958 | Kritz | 73/194 |
| 2,831,348 | 4/1958 | Kritz | 73/861.28 |
| 2,838,399 | 6/1958 | Vogel, Jr. | 99/48 |
| 2,869,357 | 11/1959 | Kritz | 73/32 |
| 2,911,825 | 11/1959 | Kritz | 73/194 |
| 2,920,012 | 1/1960 | Sanders et al. | 167/51.5 |
| 3,213,684 | 10/1965 | Seaton et al. | 73/190 |
| 3,220,255 | 11/1965 | Scranton et al. | 73/204 |
| 3,250,270 | 5/1966 | Bloom | 128/2.07 |
| 3,306,283 | 2/1967 | Arp | 128/2.07 |
| 3,523,529 | 8/1970 | Kissen | 128/2.07 |

(List continued on next page.)

FOREIGN PATENT DOCUMENTS

| | | |
|---|---|---|
| 198 10 476 | 9/1998 | (DE) . |
| 0459647 | 2/1991 | (EP) . |
| 0 712 638 | 12/1995 | (EP) . |
| 2323292 | 9/1998 | (GB) . |
| WO 96/40340 | 12/1996 | (WO) . |

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise".

British Journal Of Anaesthesia, vol. 49, 1977 London (GB) pp. 575–587, J. A. Bushman et al. "Closed Circuit Anaesthesia".

IEEE Transactions On Biomedical Engineering, vol. 35, No. 9, Sep. 1988, pp. 653–659, Capek et al., "Noninvasive Measurement of Cardia Output Using Partial CO2 ReBreathing".

Clinics In Chest Medicine (Review), vol. 10, 1989, pp. 255–264, Heigenhauser et al., "Meausurement if Cardiac Output by Carbon Dioxide Rebreathing Methods".

(List continued on next page.)

Primary Examiner—Jeffrey Snay
(74) Attorney, Agent, or Firm—Gifford, Krass, Groh, Sprinkle, Anderson & Citkowski, P.C.

(57) ABSTRACT

An indirect calorimeter is disclosed which comprises a test body (18) and a computation unit (24). In use, oxygen consumption in a respirator gas flow is determined by measuring inhaled and exhaled flow rates, and exhaled flow density, such that oxygen consumption is computed as a function of the exhaled mass.

11 Claims, 2 Drawing Sheets

U.S. PATENT DOCUMENTS

| | | | |
|---|---|---|---|
| 3,527,205 | 9/1970 | Jones | 128/2.08 |
| 3,681,197 | 8/1972 | Smith | 195/63 |
| 3,726,270 | 4/1973 | Griffis et al. | 128/2.08 |
| 3,797,480 | 3/1974 | Williams | 128/2.08 |
| 3,799,149 | 3/1974 | Rummel et al. | 128/2.07 |
| 3,814,091 | 6/1974 | Henkin | 128/188 |
| 3,834,375 | 9/1974 | Sanctuary et al. | 128/2.07 |
| 3,895,630 | 7/1975 | Bachman | 128/2.07 |
| 3,938,551 | 2/1976 | Henkin | 137/613 |
| 3,962,917 | 6/1976 | Terada | 73/204 |
| 4,003,396 | 1/1977 | Fleischmann | 137/83 |
| 4,051,847 | 10/1977 | Henkin | 128/145.6 |
| 4,078,554 | 3/1978 | Lemaitre et al. | 128/2.08 |
| 4,186,735 | 2/1980 | Henneman et al. | 128/201.25 |
| 4,188,946 | 2/1980 | Watson et al. | 128/204.22 |
| 4,197,857 | 4/1980 | Osborn | 600/531 |
| 4,200,094 | 4/1980 | Gedeon et al. | 128/201.13 |
| 4,211,239 | 7/1980 | Raemer et al. | 128/716 |
| 4,221,224 | 9/1980 | Clark | 128/718 |
| 4,230,108 | 10/1980 | Young . | |
| 4,341,867 | 7/1982 | Johansen | 435/189 |
| 4,359,057 | 11/1982 | Manzella | 128/718 |
| 4,368,740 | 1/1983 | Binder | 128/718 |
| 4,386,604 | 6/1983 | Hershey | 128/718 |
| 4,428,805 | 1/1984 | Ogura et al. | 73/861.29 |
| 4,440,177 | 4/1984 | Anderson et al. | 600/532 |
| 4,444,201 | 4/1984 | Itoh | 128/716 |
| 4,463,764 | 8/1984 | Anderson et al. | 600/532 |
| 4,572,208 | 2/1986 | Cutler et al. | 128/718 |
| 4,598,700 | 7/1986 | Tamm | 128/671 |
| 4,608,995 | 9/1986 | Linnarsson et al. | 128/713 |
| 4,619,269 | 10/1986 | Cutler et al. | 128/719 |
| 4,648,396 | 3/1987 | Raemer | 600/534 |
| 4,658,832 | 4/1987 | Brugnoli | 600/532 |
| 4,753,245 | 6/1988 | Gedeon | 128/719 |
| 4,756,670 | 7/1988 | Arai | 417/43 |
| 4,781,184 | 11/1988 | Fife | 128/205.12 |
| 4,796,639 | 1/1989 | Snow et al. | 600/532 |
| 4,850,371 | 7/1989 | Broadhurst et al. | 600/532 |
| 4,856,531 | 8/1989 | Merilainen | 600/532 |
| 4,909,259 | 3/1990 | Tehrani | 600/531 |
| 4,914,959 | 4/1990 | Mylvaganam et al. | 73/861.28 |
| 4,917,108 | 4/1990 | Mault | 128/718 |
| 4,955,946 | 9/1990 | Mount et al. | 600/532 |
| 4,986,268 | 1/1991 | Tehrani | 128/204 |
| 4,998,018 | 3/1991 | Kurahashi et al. | 250/343 |
| 5,022,406 | 6/1991 | Tomlinson | 128/719 |
| 5,038,773 | 8/1991 | Norlien et al. | 128/205.23 |
| 5,038,792 | 8/1991 | Mault | 128/718 |
| 5,042,500 | 8/1991 | Norlien et al. | 600/532 |
| 5,042,501 | 8/1991 | Kenny et al. | 600/532 |
| 5,060,506 | 10/1991 | Douglas | 73/24.1 |
| 5,060,655 | 10/1991 | Rudolph | 128/716 |
| 5,060,656 | 10/1991 | Howard | 128/718 |
| 5,069,220 | 12/1991 | Casparie et al. | 128/719 |
| 5,072,737 | 12/1991 | Goulding | 128/718 |
| 5,081,871 | 1/1992 | Glaser | 73/863.23 |
| 5,095,900 | 3/1992 | Fertig et al. | 128/207.14 |
| 5,095,913 | 3/1992 | Yelderman et al. | 128/719 |
| 5,117,674 | 6/1992 | Howard | 73/31.07 |
| 5,119,825 | 6/1992 | Huhn | 600/529 |
| 5,178,155 | 1/1993 | Mault | 128/718 |
| 5,179,958 | 1/1993 | Mault | 128/718 |
| 5,214,966 | 6/1993 | Delsing | 73/861.28 |
| 5,233,996 | 8/1993 | Coleman et al. | 600/529 |
| 5,282,473 | 2/1994 | Braig et al. | 600/532 |
| 5,285,794 | 2/1994 | Lynch | 128/719 |
| 5,293,875 | 3/1994 | Stone | 128/719 |
| 5,299,579 | 4/1994 | Gedeon et al. | 600/532 |
| 5,303,712 | 4/1994 | Van Duren | 600/529 |
| 5,309,921 | 5/1994 | Kisner et al. | 600/532 |
| 5,326,973 | 7/1994 | Eckerbom et al. | 250/343 |
| 5,355,879 | 10/1994 | Brain . | |
| 5,357,972 | 10/1994 | Norlien | 128/725 |
| 5,363,857 | 11/1994 | Howard | 600/531 |
| 5,398,695 | 3/1995 | Anderson et al. | 600/532 |
| 5,402,796 | 4/1995 | Packer et al. | 128/719 |
| 5,419,326 | 5/1995 | Harnoncourt | 128/660.02 |
| 5,425,374 | 6/1995 | Ueda et al. | 600/532 |
| 5,450,193 | 9/1995 | Carlsen et al. | 356/301 |
| 5,468,961 | 11/1995 | Gradon et al. | 250/345 |
| 5,503,151 | 4/1996 | Harnoncourt et al. | 128/660.02 |
| 5,570,697 | 11/1996 | Walker et al. | 128/719 |
| 5,632,281 | 5/1997 | Rayburn | 128/719 |
| 5,645,071 | 7/1997 | Harnoncourt et al. | 128/719 |
| 5,647,370 | 7/1997 | Harnoncourt | 128/725 |
| 5,676,132 | 10/1997 | Tillotson et al. | 128/204.23 |
| 5,705,735 | 1/1998 | Acorn | 73/23.3 |
| 5,728,585 | * 3/1998 | Yamamori et al. | 436/133 |
| 5,738,106 | * 4/1998 | Yamamori et al. | 600/532 |
| 5,754,288 | 5/1998 | Yamamoto et al. | 356/301 |
| 5,782,772 | * 7/1998 | Stegmann | 600/520 |
| 5,789,660 | 8/1998 | Kofoed et al. | 73/232 |
| 5,796,009 | 8/1998 | Delsing | 73/861.28 |
| 5,800,360 | 9/1998 | Kisner et al. | 600/532 |
| 5,816,246 | 10/1998 | Mirza | 128/726 |
| 5,831,175 | 11/1998 | Fletcher-Haynes | 73/861.28 |
| 5,834,626 | 11/1998 | DeCastro et al. | 73/23.3 |
| 5,836,300 | 11/1998 | Mault | 128/204.23 |
| 5,922,610 | 7/1999 | Alving et al. | 436/116 |
| 5,932,812 | 8/1999 | Delsing | 73/861.02 |
| 5,957,858 | 9/1999 | Micheels et al. | 600/532 |
| 6,010,459 | 1/2000 | Silkoff et al. | 600/532 |
| 6,044,843 | 4/2000 | O'Neil et al. | 128/204.23 |

OTHER PUBLICATIONS

Determination Of Nitric Oxide Levels By Fluorescence Spectroscopy, Gabor G. and Allon, N. in Biochemical, Pharmacological, And Clinical Aspects Of Nitric Oxide, edited by B. A. Weissman et al, Plenum Press, New York, 1995, pp. 57.

* cited by examiner

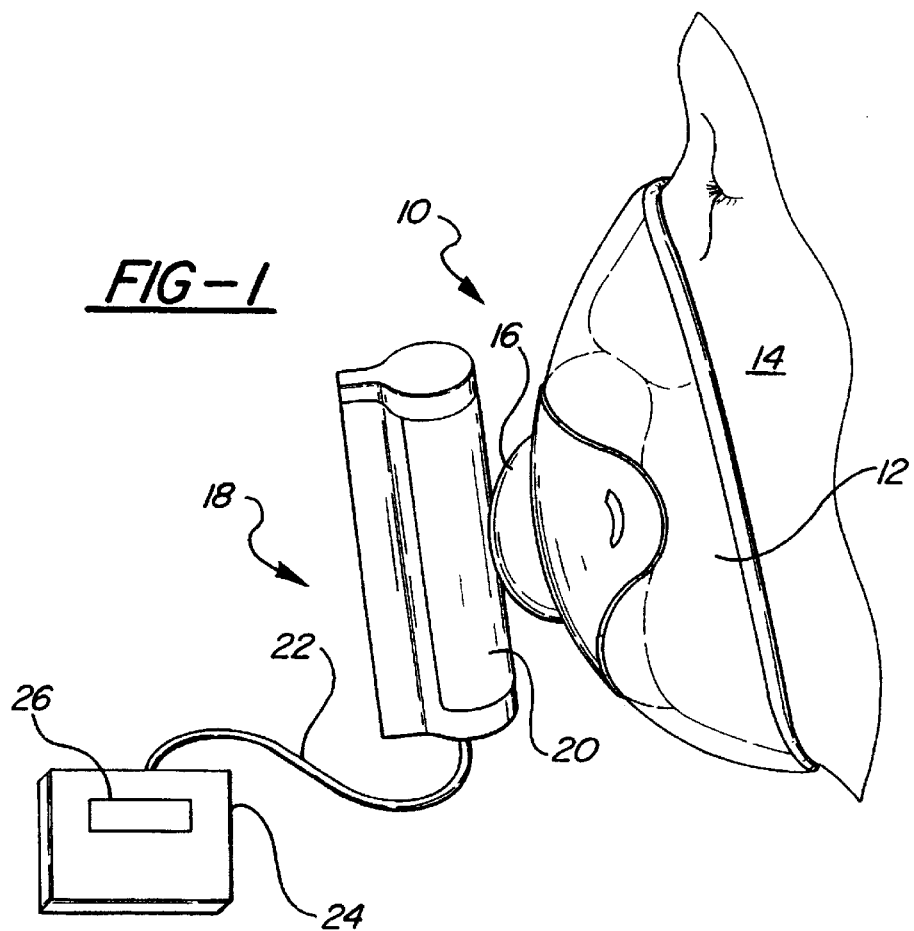
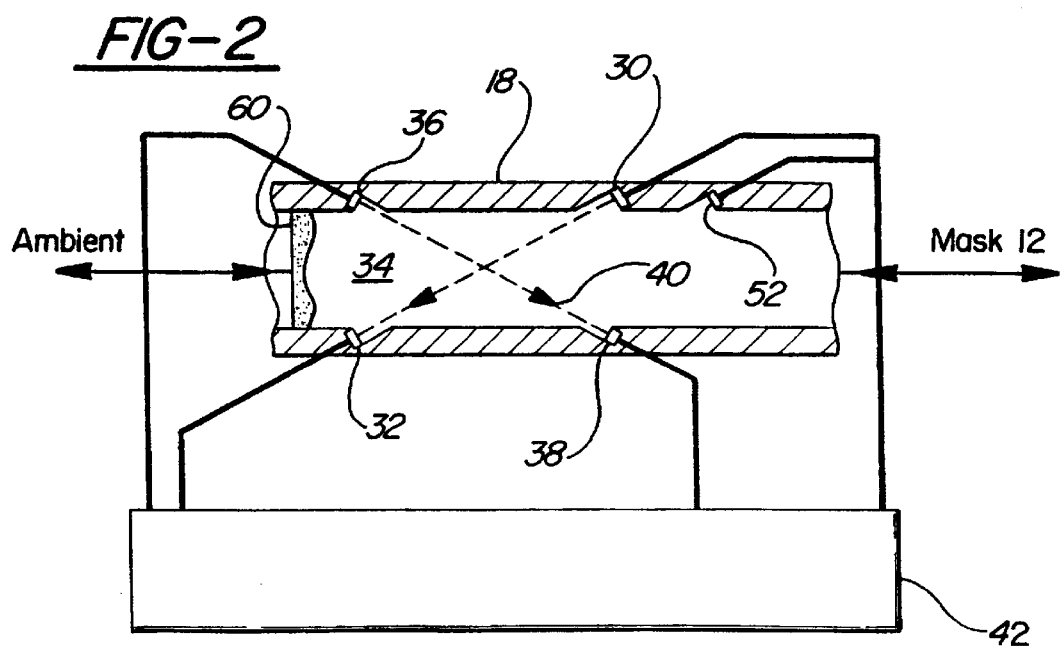

METHOD AND APPARATUS FOR RESPIRATORY GAS ANALYSIS EMPLOYING MEASUREMENT OF EXPIRED GAS MASS

This application is the National Stage of International Application No. PCT/US99/17553, filed Aug. 3, 1999, which claims the benefit of U.S. Provisional Application No. 60/095,092, filed Aug. 3, 1998.

FIELD OF THE INVENTION

This invention relates to a method and apparatus for indirect calorimetry employing respiratory gas analysis and more particularly to a method and system which determines the oxygen and/or carbon dioxide content of the expired gas using measurements of mass and volume of the expired gas and mass and volume of the inspired gas as measured by transit time of ultrasonic pulses passed through the gas.

BACKGROUND OF THE INVENTION

I have a number of patents on respiratory calorimeters. Broadly, these devices calculate the oxygen consumption of a user by subtracting the exhaled flow volume, less the exhaled $CO_2$, from the inhaled flow volume. Some of these operate by integrating the flow volume of a number of inhalations and exhalations over a period of time and by subtracting the $CO_2$ volume in the exhalation from the integral of the exhaled volume by scrubbing the $CO_2$ and then subtracting the exhaled flow volume less the $CO_2$ volume from the inhaled flow volume to determine oxygen consumption during the period. I also have a pending application that measures both inspired and expired volume and either $O_2$ or $CO_2$ content to determine oxygen consumption. The carbon dioxide scrubber is bulky and requires replenishment after a number of uses. Carbon dioxide or oxygen analyzers are also relatively expensive.

It has previously been proposed to determine the mass of a gas flowing through a conduit by determining the transit time of ultrasonic pulses passed through the gas in a direction having a component along the axis of flow so as to determine the flow rate of the gas, and additionally determining the density of the gas. U.S. Pat. No. 2,911,825 discloses such a system in which the acoustic impedance of the gas is measured to determine the density. U.S. Pat. No. 5,214,966 similarly employs the transit time of ultrasonic pulses to determine the flow rate and determines the density of the flowing gas through measurement of the velocity of sound through the gas. U.S. Pat. No. 5,645,071 uses the transit time of ultrasonic pulses to determine the flow rate and additionally makes temperature measurements which, with the flow rate, allow the determination of mass of the flowing gas. This latter patent also suggests the application of this device to pulmonary function diagnostics and discloses an additional gas analyzing sensor for determining the carbon dioxide and/or oxygen content of the flowing gas on an on-line, real time basis.

It would be desirable to provide a method of analysis which allows the determination of oxygen consumption, carbon dioxide production and related and derived respiratory factors without the need for any gas analyzers, such as $O_2$ and $CO_2$ analyzers. This would result in a low cost, high precision instrument suitable for a wide range of health care applications.

SUMMARY OF THE INVENTION

Accordingly, the present invention is directed toward a method and apparatus for analyzing respiratory gases to determine oxygen consumption for indirect calorimetry purposes as well as $CO_2$ production and related respiratory factors, by measuring the mass and flow volume of expired gas without the need for direct measurement of the oxygen or $CO_2$ concentration of the expired gas, through use of measurements of the inhaled gas. In its simplest form, in which the constituents of the inhaled gas are known with sufficient precision, as is the case when the subject is breathing ambient air, the $O_2$ and $CO_2$ contents of the exhaled gases may be determined from measurements of the mass and volume of the inhaled and exhaled gases. The temperature and/or humidity of the inspired and expired gases may be measured, assumed, or adjusted. In an alternate embodiment, the mass of the inhaled gas may be estimated. The measurements are preferably made by a subject breathing through the apparatus of the present invention with the measurements of the inhalations and exhalations being integrated over a measurement period.

To understand the method of the present invention and the system for implementing it, assume that the subject is breathing ambient air which has a composition of 79% nitrogen, 21% oxygen and 0.03% $CO_2$. By measuring the flow volume and gas density of the inhalations over the test period, the inhaled mass may be determined. From measurements of the integrated mass and flow volume of the exhalations the $CO_2$ and $O_2$ contents of the exhalations may be determined since the nitrogen content of the inhalations and exhalations will be the same, leaving only two unknowns. The mass of the exhaled gas will vary linearly as a function of its $CO_2$ and $O_2$ content. The determination of the $O_2$ and $CO_2$ content of the expired volume is possible because $CO_2$ has a substantially higher density than $O_2$ so that substitution of $CO_2$ in the exhaled gas for $O_2$ in the inhaled gas changes the gas mass. Once the exhaled $O_2$ volume is calculated, it is subtracted from the inspired oxygen volume to determine the oxygen consumption.

The system of the present invention preferably makes the flow measurements of the inhaled and exhaled volumes with known ultrasonic pulse transit time techniques and determines gas density with measurements such as acoustic impedance, speed of sound, or temperature. The same apparatus can measure the masses and flow volumes of the inhaled and exhaled gases.

BRIEF DESCRIPTION OF THE DRAWINGS

The invention will be further described in conjunction with the accompanying drawings, in which:

FIG. 1 is a perspective drawing of a preferred embodiment of the invention, being used by a subject to allow determination of the subject's respiratory parameters;

FIG. 2 is a cross sectional view of the flow tube forming part of the preferred embodiment of the invention, illustrating the associated electronics in block form;

DETAILED DESCRIPTION OF THE PREFERRED EMBODIMENTS

Figure 3:
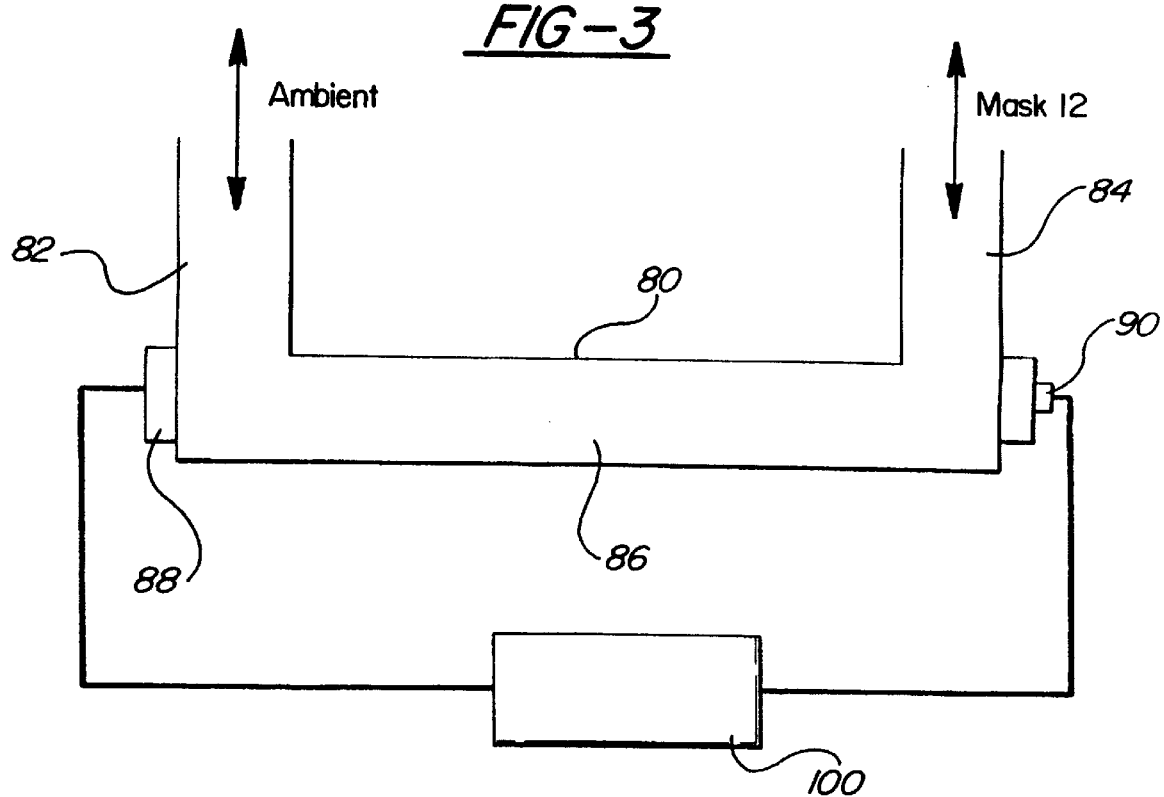
FIG. 3 is a schematic drawing of an alternative embodiment of the invention.

Referring to FIG. 1, a preferred embodiment of the invention comprises a calorimeter, generally indicated at 10, having a mask 12 formed at one end which is adapted to engage the face of a user 14 so as to cover the nose and mouth. The mask connects via a conduit 16 to a test body 18 incorporating a flow tube 20. One end of the flow tube 20 connects to the ambient air. As the user 14 inhales during a breathing test, which may last from two to ten minutes, ambient air is drawn in, passes through the flow tube 20 and to the user 14 through the mask 12. As the user exhales, air moves from the mask 12, through the conduit 16, through the flow tube 20, to the ambient air. In alternative embodiments of the invention, the source and sink for the respiratory gases may be conditioned air as used in forced respiratory apparatus.

A cable 22 connects to the test body 18 and carries electrical signals between the test body and a computation unit 24. The computation unit preferably includes a display 26 which may be switched to display the various results of the test and instructions to the user such as "start test" and "stop test." The flow tube 20 and the mask 12 are preferably formed as a disposable unit so that they may be replaced between uses for hygienic purposes. The balance of the system including the test body 18 and computation unit 24 are preferably reusable. The breath under test only passes through the disposable portions of the system.

FIG. 2 illustrates the disposable flow tube 18 in cross section. The flow tube and its associated components are of the type illustrated in U.S. Pat. No. 2,911,825 which is operative to calculate the flow rate of the inhaled and exhaled respiratory gases through the tube 18 and to calculate the density of the gases via a determination of the acoustic impedance of the flowing gases. As illustrated in FIG. 2, the left end of the flow tube 18 connects to the atmosphere so that ambient air is drawn into the flow tube when the user inhales and exhaled air is returned to the ambient. The right hand end of the flow tube connects to the mask 12. Thus, inhalations pass through the tube to the right and exhalations pass through the tube 18 to the left.

A pair of piezoelectric crystals 30 and 32 are mounted on opposite sides of the flow tube 18 at an angle to the central axis of the flow tube so that they face one another and ultrasonic pulses may be sent from the crystal 30 to the crystal 32 in the direction of the arrow 34. Similarly, a pair of crystals 36 and 38 are supported on opposite sides of the tube so that they face one another, at an angle to the central axis of the tube, in the direction of the arrow 40. Electrical connections are made from each of the crystals to an electronic control and computation circuit 42 which may be generally of the type illustrated in FIG. 1 of U.S. Pat. No. 2,911,825.

Additionally, another piezoelectric crystal transducer 52 is mounted in a wall of the flow tube 18 so as to contact the gases flowing through the tube. Signals from the transducer 30 are also provided to the computation and control unit 42. Essentially, the control unit controls the crystals 30 and 36 to transmit ultrasonic pulses to the crystals 32 and 38 respectively. The circuitry for generating the pulses and to receive the detected pulses is contained in the unit 42. Since the time of flight of these pulses between the transmitting and receiving crystals is a function of their separation and the rate of flow of gases through the tube, the flow rate may be calculated as a function of the difference between the transit times of the pulses between the two sets of crystals.

The transducer 52 forms one part of a resonance circuit controlled by an oscillator in the unit 42. The frequency of the oscillator is adjusted until the transducer 30 is tuned to series resonance and the voltage drop across the transducer 52 is measured by circuitry contained in the unit 42. This voltage is a measure of the acoustic impedance of the fluid. The density of the fluid is equal to the acoustic impedance divided by the wave propagation velocity through the fluid as fully explained in U.S. Pat. No. 2,869,357. Thus, the computation unit receives signals proportional to the flow rate of gases through the flow tube and the density of those gases and the mass can be calculated. Since the interior diameter of the flow tube 18 is known, the flow volume may be calculated.

The computation unit 42 thus measures the flow volume of the inhalations, the flow volume of the exhalations, and the mass of the exhaled volume.

The unit may incorporate a conventional artificial nose 60 which passes both the inhalations and exhalations and accumulates moisture from the exhalations and generally equalizes the temperature and humidity of the inhalations and exhalations. Alternatively, these temperatures and humidities may be measured or they may be conditioned by active elements such as a thermistor and humidifier.

Assuming that the temperature and humidity of the inhalations and exhalations are equal, the $O_2$ and $CO_2$ composition of the exhalation may easily be computed. The mass of the exhalations is first equalized on the basis of the flow volumes of the inhalations and exhalations. The mass of nitrogen in the inhalations is computed and that mass is subtracted from the mass of the exhaled gas. The remaining mass composed of $O_2$ and $CO_2$ and the mass will vary linearly depending on the proportions of those components so they can be computed or determined from a look-up table. The remaining mass is linearly related to the percentages of $CO_2$ and $O_2$ in the exhalation.

FIG. 2 illustrates the flow tube and associated circuitry of a second embodiment of the invention which uses the method and apparatus disclosed in U.S. Pat. No. 5,214,966 for the determination of the flow velocity and the sound velocity of the respiratory gases passing through the flow tube. The mass of the flowing gas may be calculated using the flow velocity and the sound velocity in the manner set forth in that patent. The flow tube 80 of the second embodiment of the invention is U-shaped with two legs 82 and 84 extending parallel to one another and at right angles to a central connecting section 86. The leg 82 connects the central section 86 to a source and sink for respiratory gases which is preferably the ambient air. The leg 84 connects the other end of the section 86 to the mask 12 illustrated in FIG. 1 or another respiratory connector such a mouthpiece.

Figure 4:
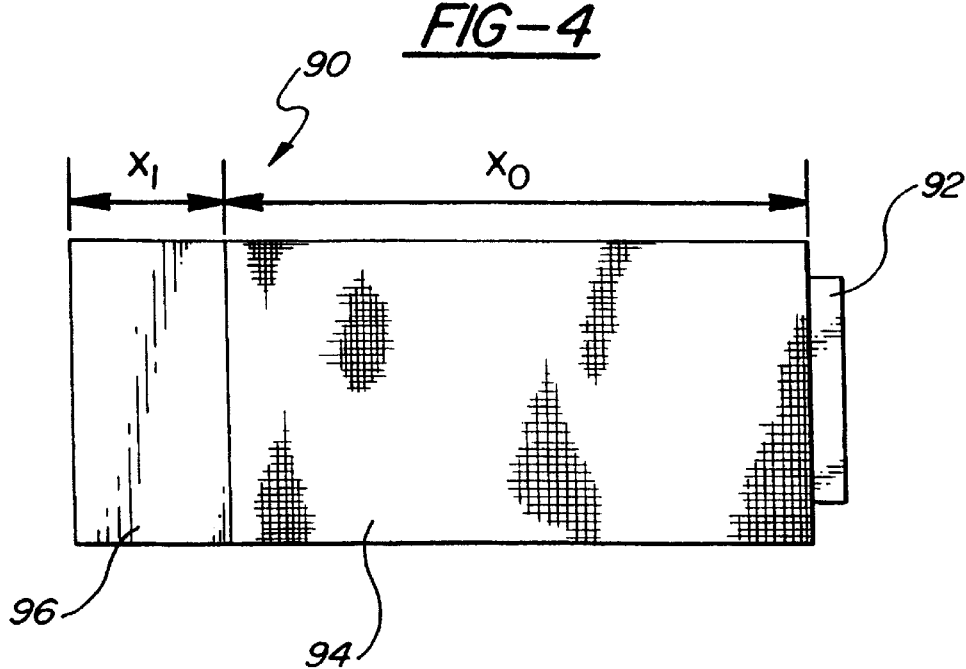
FIG. 4 is a drawing of an ultrasonic transducer capable of measuring the acoustic impedance of the flowing gas.

A first ultrasonic transducer 88 is disposed in the wall of the tube 80 at one end of the connecting section 86 in direct opposition to a second ultrasonic transducer 90 which is disposed at the opposite end so that the two face one another. Each of the two transducers 88 and 90 is formed with a piezoelectric crystal acting as both a transmitter and receiver of ultrasonic pulses. The transducer 90, which is illustrated in detail in FIG. 4, is especially designed for measuring the density of the gases flowing through the flow tube 80. As illustrated in FIG. 2, the transducer 90 consists of a piezoelectric transducer 92, a first block 94 of a material having an acoustic impedance $Z_0$ and a length $X_0$, and a second block 96 having an acoustic impedance $Z_1$, and a length $X_1$. The two blocks 94 and 96 are disposed in such a manner that an ultrasonic pulse transmitted from the crystal 92 will transverse the two blocks 94, 96 before reaching the gas. The first block 94 being disposed between and in contact with the crystal 92 and the second block 96, and the second block 96 is disposed between and in contact with the first block 94 and the gas flowing through the tube 80. The two transducers 88 and 90 are connected to a computation and control unit 100 which contains control and computation electronics.

The unit 100 includes sing-around electronic circuitry of a well known type and includes a microprocessor that calculates the flow velocity of gases passing through the section 86 of the flow tube 80.

Simultaneously, the signals from the crystal 90 are used to determine the density of the gas flowing through the section 86 based on the reflection of pulses generated by the transducer 92 from the interface between the crystals 94 and 96, the interface between the crystal 96 and the flowing gas, and the amplitude of those reflections. This is all done in the manner described in U.S. Pat. No. 5,214,966 and will not be repeated. Again, the mass of the exhalations may be calculated from the integrated flow volume density measurements. The flow volume of the inhalation may also be computed and used along with the exhaled volume to analyze the mass reading. The normalized mass will be a function of its complementary $O_2$ and $CO_2$ constituents.

In another embodiment only the expired mass and volume are measured. The expired $O_2$ concentration $[O_2]_e$ and the expired $CO_2$ concentration $[CO_2]_e$ are calculated from the expired mass and volume, and, knowing the inspired $O_2$ concentration $[O_2]_i$, then $Vo_2$ is calculated by the following formula:

$$V_{O_2} = \frac{1 - [O_2]_e - [CO_2]_e}{1 - [O_2]_i} \times ([O_2]_i - [O_2]_e) Ve \times k$$

where k is a non-adiabatic correction constant to compensate for the non-ideal nature of the gases, determinable from the van der Waals equation.

The expired volume Ve is a summation of partial volumes attributable to each of the constituent gas making up the expired volume. Since the inhaled oxygen concentration is known or determinable independent of the present invention, the volume of oxygen in the exhalant is related to the exhalant mass change associated with the molar concentrations of oxygen and carbon dioxide relative to inhalant gas. $CO_2$ volume is calculated as:

$$V_{CO_2} = [CO_2]_e \times Ve$$

Where Ve is the total expiration volume.

Having thus described my invention I claim:

1. The method of determining factors relating to oxygen consumption of a subject during a multi-breath test of the subject, comprising:
    measuring and integrating the instantaneous values of inhaled flow rate and exhaled flow rate and a factor relating to the exhaled flow density, over the time of the test to compute oxygen consumption as a function of the exhaled mass equalized by the difference between inhaled and exhaled flow volumes.

2. The method of claim 1 which uses the transit time of ultrasonic pulses through the inhaled and exhaled gases to determine flow rates.

3. The method of claim 1 in which the mass of nitrogen in the inhaled gas is computed and subtracted from the mass of exhaled gas to determine the mass of the oxygen and carbon dioxide in the exhaled gas.

4. The method of claim 3 in which the proportion of carbon dioxide and oxygen in the exhaled gas is calculated based on the combined mass of those components.

5. The method of claim 1 in which the constituents of the inhaled gases are known.

6. The method of claim 1 in which the constituents of the inhaled gases are unknown and the mass of the inhaled gas is determined from measurements of the flow rate and density of the inhaled gas.

7. The method of claim 1 further comprising equalizing the temperature and humidity of the inhaled and exhaled gases.

8. The method of claim 1 further comprising measuring or assuming the temperature and humidity of the inhaled and exhaled gases.

9. An indirect calorimeter of the type in which the inhalations and exhalations of a subject over a multi-breath test are passed through a flow tube, comprising:
    means for passing ultrasonic pulses through both inhaled and exhaled gases passing through the tube in a direction having a component parallel to the direction of flow of gases through the tube;
    means for measuring the transit times of the pulses;
    means for calculating the flow rates of the inhaled and exhaled gases from the transit times;
    means for calculating the density of the exhaled gases; and
    a computation unit for determining the oxygen consumption based on the mass of the exhalation and the inhaled and exhaled flow volumes.

10. The indirect calorimeter of claim 9 further including a transducer having a surface and contact with the flowing exhaled gases for measuring the acoustic impedance of the gases and a computation circuit operative to receive the signals proportional to the flow rate and the acoustic impedance for calculating the mass of the exhaled gases.

11. The calorimeter of claim 9 further including a temperature probe for sensing the temperature of the exhaled gases and a computation means operative to receive the output of the temperature probe and means for measuring the transit time of the pulses for computing the mass of the exhaled gases.

* * * * *